United States Patent [19]

Arena et al.

[11] Patent Number: 4,752,579

[45] Date of Patent: Jun. 21, 1988

[54] MONOSACCHARIDES FROM CORN KERNEL HULLS BY HYDROLYSIS

[75] Inventors: Blaise J. Arena; Paul Allenza, both of Des Plaines, Ill.

[73] Assignee: UOP Inc., Des Plaines, Ill.

[21] Appl. No.: 789,805

[22] Filed: Oct. 21, 1985

[51] Int. Cl.[4] .................. C12P 19/14; C12P 19/02; C13K 1/02

[52] U.S. Cl. ..................... 435/99; 435/105; 435/162; 127/37

[58] Field of Search ............ 435/99, 105, 162, 163, 435/209; 127/37

[56] References Cited

U.S. PATENT DOCUMENTS

| | | | |
|---|---|---|---|
| 4,089,745 | 5/1978 | Antrim et al. | 435/99 |
| 4,237,226 | 12/1980 | Gretlein | 435/99 |
| 4,266,981 | 5/1981 | Tsao et al. | 435/99 X |

OTHER PUBLICATIONS

Whistler et al, J.A.C.S., vol. 77, pp. 6328–6330 (1955).

*Primary Examiner*—Lionel M. Shapiro
*Attorney, Agent, or Firm*—Thomas K. McBride; John F. Spears, Jr.; Eugene I. Snyder

[57] ABSTRACT

Corn kernel hulls are found to be an essentially lignin-free material which is readily hydrolyzed to a mixture principally of three monosaccharides: D-glucose, D-xylose, and L-arabinose. Several discrete processing methods employing a combination of acid and enzymatic hydrolysis afford product streams rich either in glucose or in a mixture of the two pentoses, D-xylose and L-arabinose.

7 Claims, 1 Drawing Sheet

MONOSACCHARIDES FROM CORN KERNEL HULLS BY HYDROLYSIS

BACKGROUND OF THE INVENTION

Monosaccharides generally find broad use in commerce, and of the monosaccharides glucose in particular finds varied usage. Glucose is used as the chief substrate in fermentation media for production of ethanol, is isomerized to afford fructose, which is broadly used as a sweetener, and is itself used as a sweetener, especially in confectionary products, although glucose is only perhaps three-fourths as sweet as sugar.

A major source of glucose is cellulose, a polysaccharide of cellobiose, which is the (1→4)-linked disaccharide of beta-D-glucose. In the United States corn cobs are a major source of cellulose, for cobs are an abundant waste material resulting from one of the largest agricultural crops. The use of corn cobs is not without disadvantages which arise chiefly from the presence of lignin. Corn cobs are within the class known as lignocellulosics, where cellulose is embedded in a matrix of amorphous lignin and hemicellulose. Pretreatment of lignocellulosics is necessary to disrupt the lignin matrix so that cellulose becomes more available to subsequent hydrolytic agents, and a whole class of processes are directed toward removal of lignin from lignocellulosics. The disadvantages of delignifying pretreatments are amplified by the relatively low value of lignin and the need to dispose of the chemical waste arising from the delignification process.

In the context of glucose production it would be highly advantageous either to develop a more efficient, less costly delignification process, or to find an essentially lignin-free source of cellulose. Such a source would be desirably available in abundance and by-products accompanying glucose production would be of distinct commercial value so that the source could be efficiently used with a minimum of waste disposal problems. We have found such a source of cellulose in corn kernel hulls, a waste product of corn milling operations, which contain little or no lignin. Consequently, corn kernel hulls can be hydrolyzed in high yield without any delignifying pretreatment to afford a mixture which is mainly D-glucose, D-xylose, and L-arabinose. The latter two monosaccharides, which are pentoses, have independent utility as components of culture and fermentation media for some microorganisms, with D-xylose also being used in dyeing and tanning, so that virtually all the monosaccharides arising from hydrolysis have a commercial niche, a circumstance with important economic advantages.

Recognizing the advantages accruing from an abundant source of cellulose which requires no delignification pretreatment to make cellulose available to hydrolytic agents, we have developed several variants on a theme of hydrolyzing corn kernel hulls to a mixture of monosaccharides. In one variant acid hydrolysis at elevated temperature followed by enzymatic hydrolysis affords a maximum yield of glucose and total monosaccharides. A second variation employs acid hydrolysis at lower temperature to afford a solution whose monosaccharides are chiefly those from hemicellulose, with subsequent enzymatic hydrolysis cleaving cellulose to liberate glucose. A third variation features a very mild base pretreatment followed by enzymatic hydrolysis of cellulose to afford a solution whose monosaccharide is virtually exclusively glucose, and further acid treatment then hydrolyzes the hemicellulose component. Each variant exhibits particular advantages recommending its use, depending upon the marketplace and the needs of the processor, making the theme especially harmonious. Each variant also has unique features discovered during its development which may be indigenous to the use of corn kernel hulls as a feedstock. The remainder of this specification will be devoted to the exposition of the underlying theme and the development of its different variations.

SUMMARY OF THE INVENTION

The purpose of this invention is to develop a method of making D-glucose, D-xylose, and L-arabinose, in combination or either one alone, from a readily abundant material without the need for any delignifying pretreatment. An embodiment comprises hydrolyzing corn kernel hulls with acid at elevated temperature with subsequent enzymatic hydrolysis of the hydrolysate. In a more specific embodiment acid hydrolysis is conducted at a temperature from about 85° to about 110° C. In another embodiment corn kernel hulls are hydrolyzed with acid at a temperature less than about 75° C. to afford a mixture of pentoses which may be separately recovered, followed by enzymatic hydrolysis to afford glucose from the unhydrolyzed cellulose. In yet another embodiment a mild base pretreatment of corn kernel hulls is followed by enzymatic hydrolysis to afford glucose as the substantially exclusive monosaccharide, with subsequent acid hydrolysis of the hemicellulose and unreacted cellulose components. Other embodiments and features will be readily apparent from the following description.

DESCRIPTION OF THE INVENTION

Our invention arises from several discrete discoveries. The basic one, from the corn wet milling industry is that corn kernel hulls contain little if any lignin. A typical analysis of corn kernel hulls shows about 20% starch, about 30% cellulose, about 30% hemicellulose, about 10% protein, and less than 5% lignin. Consequently, corn kernel hulls act differently from typical lignocellulosics in not requiring delignification in order to hydrolyze the cellulose and hemicellulose components. Secondly, we have discovered that in the acid hydrolysis of corn kernel hulls the yield of glucose is quite temperature dependent, whereas the yield of the pentoses, D-xylose and L-arabinose, is relatively invariant. This permits a degree of control of hydrolysate content not heretofore appreciated. We also have discovered that a relatively mild base pretreatment suffices to disrupt the crystallinity of cellulose in corn kernel hulls to a degree where it is susceptible to enzymatic hydrolysis. The combination of two or more of these discoveries affords variants of hydrolytic processes which are described and claimed within.

One noteworthy feature of our invention is its flexibility; each process scheme has options which permits the processor to take advantage of current market conditions. Another noteworthy feature of our invention is that some of its options inherently lead to separation of the monosaccharide hydrolysis products into hexose and pentose streams without necessitating a separate and distinct separations stage other than simple filtration.

Figure 1:
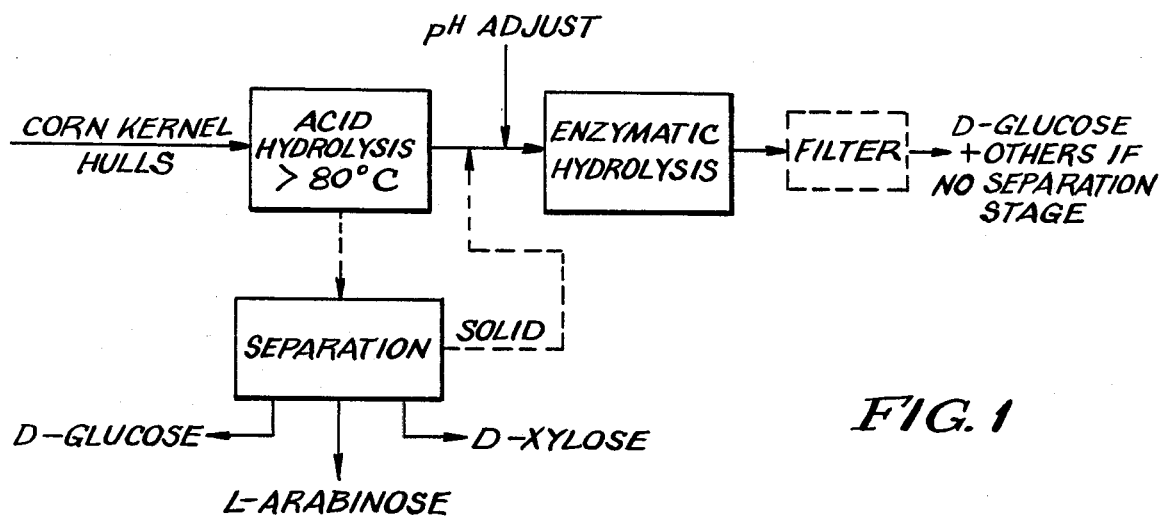
FIG. 1 is a flow scheme for hydrolysis of corn kernel hulls using sequentially strong acid at a temperature over 80° C. followed by enzymatic hydrolysis, with an optional separation stage after acid hydrolysis.

A flow scheme for our first variant is depicted in FIG. 1. In this variant corn kernel hulls are hydrolyzed by sequentially subjecting the hulls to hydrolysis with a strong acid at a temperature in the range from about 80° to about 110° C., then subjecting the acid hydrolysate to hydrolysis with a cellulose-degrading enzyme, and recovering the resulting enzymatic hydrolysate. Among the strong acids which may be used in the initial acid hydrolysis are sulfuric acid, hydrochloric acid, phosphoric acid, hydrofluoric acid, trifluoroacetic acid, trichloroacetic acid, and so on. The particular nature and identity of the strong acid used is not important so long as it is not an oxidizing acid under reaction conditions. Acid concentrations typically are in the range from about 0.5% to about 15% by weight, and more typically are in the 3% to 10% by weight range.

Hydrolysis with strong acid is carried out between about 80° and about 110° C. The maximum temperature is dictated by the observation that at temperatures in excess of about 110° C. appreciable degradation of the hydrolysate may occur. The minimum temperature is dictated by the observation that glucose yields are quite temperature dependent, requiring inordinately long reaction times at lower temperatures to attain maximum glucose production. A temperature range between about 95° and about 105° C. appears to be optimal.

The reaction product from acid hydrolysis is then treated with a cellulose-degrading enzyme to complete the hydrolysis of unreacted cellulose. The enzyme cellulase is commonly used at a temperature between about 25° and about 55° C., preferably between about 35° and about 50° C. Generally, the mixture is buffered to a pH from about 3 to about 6, more commonly in the range from 4.0 to about 5.0. When enzymatic hydrolysis is complete the resulting hydrolysate is recovered and processed according to the needs of the manufacturer. Thus, glucose may be separated from the pentoses, the monosaccharides separated from all other components, or, perhaps, the entire hydrolysate can be used as such without further processing.

In a subvariant the reaction product from acid hydrolysis is separated into a liquid portion and a solid portion. Separation may be by any convenient means, such as by membrane separation or by simple filtration. Separation by filtration is preferred, and where practiced it is important to not dry the filter cake prior to its subsequent use as described below. The monosaccharides of the liquid portion are chiefly D-glucose, D-xylose, and L-arabinose, and the liquid portion may be separately processed to isolate and purify one or more of the constituent monosaccharides. The solid portion obtained in separation is then subjected to enzymatic hydrolysis. The hydrolysate therefrom is recovered and is found to contain chiefly D-glucose.

The subvariant described above is preferred where the maximum total glucose yield is desired. That is, the subvariant as described affords a greater total glucose yield than if no separation of liquid and solid from strong acid hydrolysis is practiced. The subvariant also affords an enzymatic hydrolysate which contains D-glucose virtually exclusively as the sole soluble monosaccharide, thereby facilitating its ease of purification. Accordingly, the subvariant may be advantageously practiced where a relatively pure D-glucose stream is desired.

Figure 2:
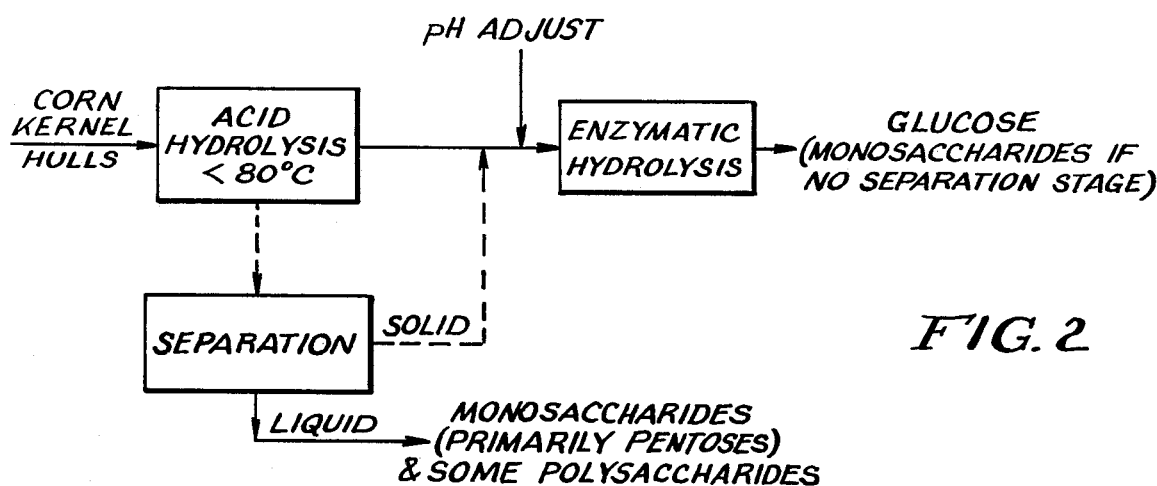
FIG. 2 is a flow scheme for hydrolysis of corn kernel hulls using sequentially strong acid at a temperature under 80° C. followed by enzymatic hydrolysis, with an optional separation stage after acid hydrolysis.

The second variation, whose flow scheme is given in FIG. 2, is similar to the sequential acid-enzyme hydrolysis process described above except that acid hydrolysis is conducted at a temperature less than about 80° C. The reason for this rests on the observation that acid hydrolysis of corn kernel hulls at lower temperature affords a mixture rich in the pentoses and with relatively low glucose content, and hence affords a selectivity unattainable at higher temperatures. As stated above, in this variant acid hydrolysis is conducted at a temperature less than about 80° C., preferably in the range from about 35° to about 70° C., and more particularly in the range from about 40° to about 60° C. The acids which may be used and the concentration at which they are used is the same as that described above. Similarly, subsequent treatment of the acid hydrolysate with a cellulose-degrading enzyme is the same as that previously described.

In a subvariant of this method the acid hydrolysate is separated into a liquid portion and a solid portion. As previously mentioned, separation may be by any convenient means, such as membrane separation or filtration, and simple filtration is preferred. The liquid portion consists mainly of monosaccharides, chiefly D-xylose and L-arabinose, as well as some soluble polysaccharides. The solid portion is then resuspended and subjected to enzymatic hydrolysis by a cellulose-degrading enzyme. The resulting hydrolysate contains chiefly D-glucose as its sole monosaccharide.

It is readily seen that the subvariant affords two quite distinct product streams. The liquid portion from separation of the acid hydrolysate contains chiefly pentoses, with some soluble polysaccharides, whereas the enzymatic hydrolysate contains chiefly glucose as its monosaccharide. It thus has the advantages of affording a facile separation between pentoses on the one hand and D-glucose on the other hand. However, it also needs to be recognized that when the subvariant is practiced, the *total* glucose yield is reduced, probably because some polysaccharides remain dissolved in the liquid portion of the separated hydrolysate stream.

Figure 3:
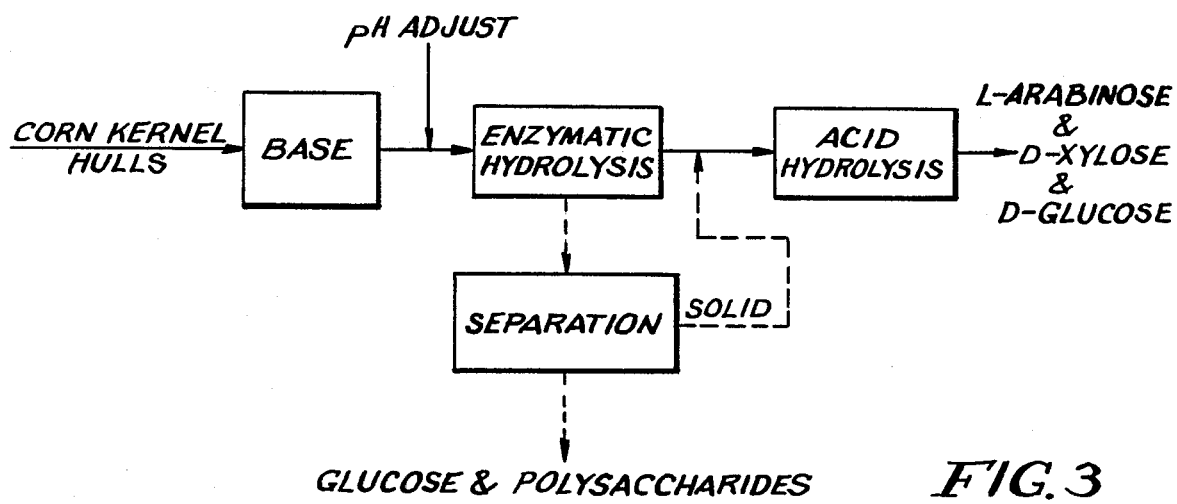
FIG. 3 is a flow scheme for hydrolysis of corn kernel hulls using a mild base pretreatment followed first by enzymatic hydrolysis, then acid hydrolysis, with an optimal separation stage after enzymatic hydrolysis.

In yet another variation represented by FIG. 3 the corn kernel hulls are mixed with a dilute solution of a strong base at a temperature between about 10° and about 40° C., and then sequentially hydrolyzed first by a cellulose-degrading enzyme and thereafter by a strong acid, and recovering the resulting hydrolysate. The purpose of the base pretreatment is to reduce the crystallinity of cellulose so that it becomes more susceptible to enzymatic hydrolysis.

It will be appreciated that the base pretreatment is unusually mild by comparison to similar treatments for lignocellulosic materials. The identity of the base is unimportant, and such bases as alkali metal hydroxides and carbonates frequently will be employed for convenience. Sodium hydroxide, potassium hydroxide, lithium hydroxide, sodium carbonate, potassium carbonate, lithium carbonate, and mixtures thereof are examples of suitable bases which will be used at a concentration from about 0.5% to about 5%, and generally in the range between about 0.5% and about 3%. The base pretreatment is conducted at a temperature between about 10° and about 40° C., generally between about 15° and 30° C., for a time sufficient to achieve its stated purpose. Base pretreatment time will vary with such factors as contact efficiency between the corn kernel hulls and base, temperature, concentration of base, and so forth, but typically will be in the range from about 15 to about 180 minutes.

The material resulting from base pretreatment, without any filtration, is subjected to hydrolysis using a cellulose-degrading enzyme under conditions previously described. The enzymatic hydrolysate is then hydrolyzed with strong acid as described above to afford the final product stream.

As in the other two variations, this one also has a subvariant in which the enzymatic hydrolysate is separated into a liquid portion and a solid portion. The liquid portion, which can be obtained by such separation methods as membrane separation and simple filtration, contains D-glucose as virtually the exclusive monosaccharide and some soluble polysaccharides. Consequently, use of this subvariant affords a relatively pure D-glucose stream.

The solid portion is thereafter subjected to hydrolysis with a strong acid, with the acid hydrolysate containing chiefly D-glucose, D-xylose, and L-arabinose. However, because there are some dissolved polysaccharides in the liquid portion of the separation stage the total yield of monosaccharides from this subvariant is less than that where no separation is applied to the enzymatic hydrolysate, and may not be advantageous where yield maximization is important.

The following examples are merely illustrative of our invention and it is not intended to limit it thereby.

EXAMPLE 1

Acid hydrolysis of corn kernel hulls; effect of temperature on monosaccharide distribution. A 15 g sample of corn kernel hulls, obtained as the "expeller output" from a major corn milling operator, was mixed with 200 ml of 7% sulfuric acid for 5.5–6.0 hrs. at varying temperatures. The reaction mixture then was cooled, filtered, and the filter cake washed with about 100 ml water. The filter cake represented about 25% by weight of starting material. The filtrate was analyzed for glucose, xylose, and arabinose by HPLC with the results summarized in Table 1.

TABLE 1

| Effect of Temperature in Acid Hydrolysis | | | | |
| --- | --- | --- | --- | --- |
| Time, hr. | 5.5 | 6 | 6 | 5.5 |
| T, °C. | 100 | 85 | 70 | 60 |
| Wt. % Sample Hydrolyzed to: | | | | |
| Glucose | 29.8 | 24.9 | 12.3 | 3.3 |
| Xylose | 14.8 | 13.6 | 14.4 | 8.3 |
| Arabinose | 10.3 | 9.0 | 10.3 | 11.6 |

These results show that the extent of glucose formation is quite temperature dependent. At temperatures between 70° and 100° C. both xylose and arabinose content appear unaffected by temperature. At 60° C. and below the xylose yield also decreases.

EXAMPLE 2

Strong acid hydrolyis at elevated temperature. Corn kernel hulls were hydrolyzed in 7% sulfuric acid at 100° C. for 5.5 hrs. In Run A the acid hydrolysate was filtered and the filter cake was washed, with the washings added to the filtrate, dried, then resuspended in an acetate buffer, 0.1 molar, at pH 4.5, and hydrolyzed with 0.4% cellulase for 24 hrs. at 45° C. In Run B the acid hydrolysate was filtered, the filter cake was washed with the washings added to the filtrate, and the filter cake then suspended in an acetate buffer without being prior dried. The suspension was then enzymatically hydrolyzed as in A. In Run C the acid hydrolysate was not filtered but instead adjusted to pH 4.5, acetate buffer was added as previously described and the mixture enzymatically digested. The results are summarized in Table 2.

TABLE 2

| Acid Hydrolysis at Elevated Temperature | | | | | | |
| --- | --- | --- | --- | --- | --- | --- |
| Run | Material | Enzyme Glucose | Acid Glucose | Xylose | Arab- inose | Total Glu- cose |
| A | filtrate from acid hydrolysate | | 26.9 | 14.9 | 10.5 | |
| | cellulase hydrolysate | 1.2 | | | | 28.1 |
| B | filtrate from acid hydrolysate | | 25.0 (25.5)$^a$ | 18.6 (14.8) | 9.7 (10.6) | |
| | cellulase hydrolysis | 14.0 | | | | 39.5 |
| C | acid hydrolysate | | 23.5 | 13.7 | 9.8 | |
| | cellulase hydrolysate | 8.8$^b$ | | | | 32.3 |

$^a$Figures in parenthesis represent duplicate run.
$^b$Figures represent incremental glucose production.
$^c$Figures for monosaccharides are weight percent based on total corn hulls used.

These results show that for maximization of glucose content filtration of the acid hydrolysate is required, but the filter cake should not be dried prior to enzymatic hydrolysis.

EXAMPLE 3

Acid hydrolysis at lower temperature. A mixture of 14.9 dried corn kernel hulls and 200 ml of 7% sulfuric acid were heated at 60° C. for 5.5 hours. The cooled mixture was filtered and the cake was washed with about 100 ml of water. Analysis of the combined washings and filtrate showed they contained 2.5% glucose, 8.4% xylose, and 10.1% arabinose based on the initial weight of hulls.

The filter cake was suspended in about 250 ml distilled water and the pH was adjusted to 4.8. After acetate buffer at pH 4.8 (1 molar, 30 ml) and 1.2 g cellulase were added the volume was adjusted to 300 ml. After the mixture was incubated on a shaker at 45° C. for 24 hours it was filtered, the filter cake amounting to 9.8% by weight of the hulls. Analysis of the filtrate showed it contained 17.4% glucose and under 1% of other monosaccharides based on initial hull weight.

EXAMPLE 4

Mild base pretreatment. Samples of corn kernel hulls were mixed with a solution of 1.5% sodium hydroxide (75 ml base per 5 g hulls) at ambient temperature for about 90 minutes. The mixture was adjusted to pH 4.5, acetate buffer at the same pH was added to 0.1 molar concentration, and the mixture was digested with 0.4% (W/V) cellulase for 24 hours at 45° C. In Run A the enzyme hydrolysate was filtered and washed, with the washings added to the filtrate, and the filter cake was subjected to acid hydrolysis at 100° C. as described in Example 3. In Run B the enzyme hydrolysate was not filtered, but the entire hydrolysate was subjected to acid hydrolysis as previously described. Results are tabulated below, with monosaccharides given in weight percent based on hulls used.

TABLE 4

Mild Base Pretreatment of Corn Kernel Hulls

| Run | Material | Enzyme Glucose | Acid Glucose | Xylose | Arabinose | Total Glucose |
|---|---|---|---|---|---|---|
| A | filtrate from enzyme hydrolysate | 34 | | | | |
| | acid hydrolysate | | 0.6 | 1.3 | 0.7 | 34.6 |
| B | enzyme hydrolysate · | 34 | | | | |
| | acid hydrolysate[a] | | 5 | 17.5 | 10.5 | 39 |

[a] figures represent incremental monosaccharide production.

These results show that a rather pure glucose stream can be obtained by enzymatic hydrolysis of a mildly base-treated corn hull feedstock. They also show that the enzyme-treated material should not be filtered prior to acid hydrolysis for maximum monosaccharide formation. Other data also demonstrate that the initial base-digested material should not be filtered prior to enzymatic hydrolysis, for if only the filtrate is treated with enzyme the glucose yield is reduced to 15% from the 34% obtained without filtration.

What is claimed is:

1. A method of hydrolyzing corn kernel hulls comprising mixing the hulls with a dilute solution of a strong base at a temperature between about 10° and about 40° C., then sequentially subjecting the base-treated hulls to hydrolysis by a cellulose-degrading enzyme followed subjecting the enzymatic hydrolysate to acid hydrolysis with a strong acid, and recovering the resulting hydrolysate.

2. The method of claim 1 further characterized in that the enzymatic hydrolysate is separated into a liquid portion, whose monosaccharide is chiefly D-glucose, and a solid portion said solid portion thereafter being subjected to hydrolysis with a strong acid, and recovering the acid hydrolysate containing chiefly D-glucose, D-xylose, and L-arabinose.

3. The method of claim 1 where the enzyme is cellulase.

4. The method of claim 1 where the enzymatic hydrolysis is conducted at a temperature between about 35° and about 55° C. and a pH between about 3 to about 6.

5. The method of claim 1 where the hulls are pretreated with a solution containing from 0.5 to about 3.0 weight-volume percent of a strong base.

6. The method of claim 1 where the temperature is between about 15 and about 30° C.

7. The method of claim 1 further characterized in that the retreating of the hulls is performed for a time for about 15 minutes to about 3 hours.

* * * * *

UNITED STATES PATENT AND TRADEMARK OFFICE
CERTIFICATE OF CORRECTION

PATENT NO. : 4,752,579
DATED : June 21, 1988
INVENTOR(S) : Arena et al.

It is certified that error appears in the above-identified patent and that said Letters Patent is hereby corrected as shown below:

In Column 8, line 6: After "followed" insert --by--.

Signed and Sealed this

Eighth Day of November, 1988

Attest:

DONALD J. QUIGG

Attesting Officer

Commissioner of Patents and Trademarks